(12) United States Patent
Buckland

(10) Patent No.: US 12,658,308 B2
(45) Date of Patent: *Jun. 16, 2026

(54) METHODS, SYSTEMS AND COMPUTER PROGRAM PRODUCTS FOR RETROSPECTIVE DATA MINING

(71) Applicant: Translational Imaging Innovations, Inc., Hickory, NC (US)

(72) Inventor: Eric L. Buckland, Hickory, NC (US)

(73) Assignee: Translational Imaging Innovations, Inc., Hickory, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/628,901

(22) Filed: Apr. 8, 2024

(65) Prior Publication Data

US 2024/0347173 A1    Oct. 17, 2024

Related U.S. Application Data

(63) Continuation of application No. 17/272,472, filed as application No. PCT/US2019/049472 on Sep. 4, 2019, now Pat. No. 11,955,227.

(Continued)

(51) Int. Cl.
*H04W 4/18* (2009.01)
*G06F 9/54* (2006.01)
(Continued)

(52) U.S. Cl.
CPC ............. *G16H 30/40* (2018.01); *G06F 9/547* (2013.01); *G06F 16/284* (2019.01);
(Continued)

(58) Field of Classification Search
CPC ...... G06F 3/1275; G06F 9/445; G06F 16/901; G06F 16/907; G06F 16/9536;
(Continued)

(56) References Cited

U.S. PATENT DOCUMENTS

| | | |
|---|---|---|
| 5,867,602 A | 2/1999 | Zandi et al. |
| 5,999,911 A | 12/1999 | Berg et al. |

(Continued)

FOREIGN PATENT DOCUMENTS

| | | |
|---|---|---|
| CN | 106682530 A | 5/2017 |
| JP | 2018 133080 A | 8/2018 |

(Continued)

OTHER PUBLICATIONS

Abràmoff, M. D., Lavin, P. T., Birch, M., Shah, N. & Folk, J. C. Pivotal trial of an autonomous AI-based diagnostic system for detection of diabetic retinopathy in primary care offices. *npj Digit. Med.* 1, 39 (2018).

(Continued)

*Primary Examiner* — Quan M Hua
(74) *Attorney, Agent, or Firm* — Stanek Lemon Crouse & Meeks, PA

(57) ABSTRACT

An integrated system for processing and using images acquired of subjects in a research or clinical environment is provided. The integrated system includes an image and data bank, a workflow management module, a cloud storage module and a pre-processing module. The pre-processing engine is positioned between the workflow management module and the cloud storage module and is configured to receive raw images, data associated with the raw images and the data associated with the imaged subjects from the workflow management module and process this data and provide the processed data to be pushed into the cloud storage module. The pre-processing engine also anonymized the data to provide de-identified images and data to the cloud storage module and create a key that relates the raw images, data associated with the raw images and the data associated with the imaged subjects to the de-identified, processed images and data. The key remains separate and un-con- (Continued)

nected from the de-identified, processed images and data. The key allows the de-identified, processed images and data to maintain traceability to the imaged subjects and to all subsequent operations on the images and data.

1 Claim, 9 Drawing Sheets

Related U.S. Application Data

(60) Provisional application No. 62/727,072, filed on Sep. 5, 2018.

(51) Int. Cl.

| | |
|---|---|
| *G06F 16/28* | (2019.01) |
| *G06F 21/62* | (2013.01) |
| *G06T 7/00* | (2017.01) |
| *G16H 30/40* | (2018.01) |
| *H04L 67/10* | (2022.01) |
| *H04L 67/12* | (2022.01) |

(52) U.S. Cl.
CPC ........ *G06F 21/6245* (2013.01); *G06T 7/0012* (2013.01); *G06T 2207/20081* (2013.01); *G06T 2207/30041* (2013.01); *H04L 67/10* (2013.01); *H04L 67/12* (2013.01)

(58) Field of Classification Search
CPC ........ G16B 40/00; G16B 40/30; G16B 45/00; G16B 20/00; G16H 30/40; G16H 20/40; G16H 40/20; G11B 27/34; H04N 1/00204; G06T 2207/20084; G06T 2207/20208; G06T 7/248; G06T 7/285; G06V 10/776; G06V 10/82; G06V 10/95; G06V 20/40; G06V 20/52; G06V 20/54
See application file for complete search history.

(56) References Cited

U.S. PATENT DOCUMENTS

| | | | |
|---|---|---|---|
| 6,058,215 A | 5/2000 | Schwartz et al. | |
| 6,891,973 B1 | 5/2005 | Atsumi et al. | |
| 6,904,161 B1 | 6/2005 | Becker et al. | |
| 6,937,767 B1 | 8/2005 | Burak et al. | |
| 6,996,549 B2 | 2/2006 | Zhang et al. | |
| 7,024,046 B2 | 4/2006 | Dekel et al. | |
| 7,218,789 B2 | 5/2007 | Faber et al. | |
| 7,471,850 B2 | 12/2008 | Srinivasan | |
| 7,519,591 B2 | 4/2009 | Landi et al. | |
| 8,583,466 B2 | 11/2013 | Margulies et al. | |
| 8,682,910 B2 | 3/2014 | Fu et al. | |
| 8,694,646 B1 | 4/2014 | Kothari et al. | |
| 8,867,807 B1 | 10/2014 | Fram ..................... | G16H 30/20 |
| | | | 382/128 |
| 8,879,813 B1 | 11/2014 | Solanki et al. | |
| 9,135,320 B2 | 9/2015 | Goyal et al. | |
| 9,147,179 B2 | 9/2015 | Syeda-Mahmood et al. | |
| 9,324,022 B2 | 4/2016 | Williams, Jr. et al. | |
| 9,355,273 B2 | 5/2016 | Stevens et al. | |
| 9,395,959 B2 | 7/2016 | Hatfield et al. | |
| 9,589,374 B1 | 3/2017 | Gao et al. | |
| 9,635,000 B1 | 4/2017 | Muftic | |
| 9,760,807 B2 | 9/2017 | Zhou et al. | |
| 9,767,307 B2 | 9/2017 | Cismas | |
| 9,846,938 B2 | 12/2017 | Steigauf et al. | |
| 10,140,421 B1 | 11/2018 | Bernard et al. | |
| 10,515,128 B2 | 12/2019 | Kurian | |
| 11,955,227 B2 * | 4/2024 | Buckland ........... | G06F 21/6245 |
| 2004/0122790 A1 | 6/2004 | Walker et al. | |
| 2006/0285730 A1 | 12/2006 | Habets et al. | |
| 2007/0067252 A1 * | 3/2007 | Hengerer ............... | G16H 30/20 |
| 2009/0171708 A1 | 7/2009 | Bobak et al. | |

| | | | |
|---|---|---|---|
| 2010/0049740 A1 | 2/2010 | Iwase et al. | |
| 2010/0070306 A1 | 3/2010 | Dvorak et al. | |
| 2010/0174558 A1 | 7/2010 | Smith et al. | |
| 2010/0241990 A1 | 9/2010 | Gabriel et al. | |
| 2011/0110568 A1 | 5/2011 | Vesper et al. | |
| 2013/0144678 A1 | 6/2013 | Ramachandran | |
| 2013/0208955 A1 | 8/2013 | Zhao et al. | |
| 2013/0208966 A1 | 8/2013 | Zhao et al. | |
| 2014/0142984 A1 | 5/2014 | Wright et al. | |
| 2014/0153808 A1 | 6/2014 | Wu et al. | |
| 2014/0350954 A1 | 11/2014 | Ellis et al. | |
| 2015/0149208 A1 | 5/2015 | Lynch et al. | |
| 2015/0332283 A1 | 11/2015 | Witchey | |
| 2016/0092721 A1 | 3/2016 | Kanagasingam et al. | |
| 2016/0330027 A1 | 11/2016 | Ebrahimi | |
| 2017/0076043 A1 | 3/2017 | Dormer et al. | |
| 2017/0147296 A1 | 5/2017 | Kumar et al. | |
| 2017/0231594 A1 | 8/2017 | Dominick .............. | A61B 5/055 |
| | | | 600/410 |
| 2017/0300627 A1 | 10/2017 | Giordano et al. | |
| 2018/0046766 A1 | 2/2018 | Deonarine et al. | |
| 2018/0048766 A1 | 2/2018 | Deonarine et al. | |
| 2018/0068438 A1 | 3/2018 | DeVries | |
| 2018/0121620 A1 | 5/2018 | Bastide et al. | |
| 2018/0218074 A1 * | 8/2018 | Ishikawa ................ | G16H 40/67 |
| 2019/0080207 A1 | 3/2019 | Chang ................. | G06F 16/7837 |
| 2020/0211170 A1 * | 7/2020 | Coria Mendoza ..... | H04N 23/64 |
| 2021/0193297 A1 | 6/2021 | Buckland | |
| 2022/0076802 A1 | 3/2022 | Bondar et al. | |

FOREIGN PATENT DOCUMENTS

| | | |
|---|---|---|
| RU | 2256224 C1 | 10/2005 |
| WO | WO 2018/069736 A1 | 4/2018 |

OTHER PUBLICATIONS

Bach et al., "Data Anonymization patent landscape." CRORR 8 (2017), pp. 265-281.

Brainard, D. H., Cooper, R. F., Morgan, J. I. W., Tuten, W. S. & Dubra, A. Non-invasive assessment of human cone photoreceptor function: erratum. *Biomed. Opt. Express* 9, 1842 (2018).

Broadgate, S., Yu, J., Downes, S. M. & Halford, S. Unravelling the genetics of inherited retinal dystrophies: Past, present and future. *Prog. Retin. Eye Res.* 59, 53-96 (2017).

Carroll, J. et al. Effects of Intraframe Distortion on Measures of Cone Mosaic Geometry from Adaptive Optics Scanning Light Ophthalmoscopy. *Transl. Vis. Sci. Technol.* 5, 10 (2016).

CDC Vision Health Initiative Economic Studies. https://www.cdc.gov/visionhealth/projects/economic_studies.htm (2017).

Cooper, R. F. et al. Automatic detection of cone photoreceptors in split detector adaptive optics scanning light ophthalmoscope images. *Biomed. Opt. Express* 7, 2036 (2016).

Cooper, R. F., WilK, M. A., Tarima, S. & Carroll, J. Evaluating descriptive metrics of the human cone mosaic. *Investig. Ophthalmol. Vis. Sci.* 57, 2992-3001 (2016).

Cremers, F. P. M., Boon, C. J. F., Bujakowska, K. & Zeitz, C. Special issue introduction: Inherited retinal disease: Novel candidate genes, genotype-phenotype correlations, and inheritance models. *Genes (Basel)*, 9, 1-10 (2018).

Cunefare, D. et al. Deep learning based detection of cone photoreceptors with multimodal adaptive optics scanning light ophthalmoscope images of achromatopsia. *Biomed. Opt. Express* 9. 3740 (2018).

Cunefare, D. et al. Open source software for automatic detection of cone photoreceptors in adaptive optics ophthalmoscopy using convolutional neural networks, *Sci. Rep.* 7, 1-11 (2017).

Dicarlo, J. E., Mahajan, V. B. & Tsang, S. H. Gene therapy and genome surgery in the retina. *J. Clin. Invest.* 128, 2177-2188 (2018).

FDA. *Medical Device Development Tools (MDDT)*, (2019).

Gasparini, S. J., Llonch, S., Borsch, O. & Ader, M. Transplantation of photoreceptors into the degenerating retina: Current state and future perspectives. *Prog, Retin. Eye Res.* 1-37 (2018). doi:10.1016/j.preteyeres.2018.11.001.

(56) References Cited

OTHER PUBLICATIONS

Godara, P., Dubis, A. M., Roorda, A., Duncan, J. L. & Carroll, J. Adaptive optics retinal imaging: Emerging clinical applications. in *Optometry and Vision Science* 87, 930-941 (2010).

Hunter, J. J., Cookson, C. J., Kisilak, M. L., Bueno, J. M. & Campbell, M. C. W. Characterizing image quality in a scanning laser ophthalmoscope with differing pinholes and induced scattered light. *J. Opt. Soc. Am. A. Opt. Image Sci. Vis.* 24, 1284-95 (2007).

International Search Report and Written Opinion of the International Searching Authority for PCT/US2021/024834, mailed Jul. 15, 2021, 15 pages.

Kaluzny, J. et al. Hyperspectral measurement of retinal oximetry in diabetes. *Investig. Ophthalmol. Vis. Sci.* 57(12), 3743 (2016).

Kaplan, Bonnie, "Selling Health Data: De-Identification, Privacy and Speech," ISPS—Bioethics Working Paper, Oct. 7, 2014, 33 pages.

Langlo, C. S. et al. An Automated Reference Frame Selection (ARFS) Algorithm for Cone Imaging with Adaptive Optics Scanning Light Ophthalmoscopy. *Transl. Vis. Scl. Technol.* 6, 9 (2017).

Litts, K. M., Cooper, R. F., Duncan, J. L. & Carroll, J. Photoreceptor-Based Biomarkers in AOSLO Retinal Imaging. *Invest. Ophthalmol. Vis. Sci.* 58, BIO255-BIO267 (2017).

Mantha, S., Roizen, M. F., Fleisher, L. A., Thisted, R. & Foss, J. Comparing methods of clinical measurement: Reporting standards for bland and altman analysis. *Anesth. Analg.* 90, 593-602 (2000).

Martin Bland, J. & Altman, D. Statistical Methods for Assessing Agreement Between Two Methods of Clinical Measurement. *Lancet* 327, 307-310 (1986).

Office Action, U.S. Appl. No. 13/668,509, filed Apr. 4, 2018, 22 pages.

Ourselin, S. et al. Automatic Cone Photoreceptor Localisation in Healthy and Stargardt Afflicted Retinas Using Deep Learning. *Sci. Rep.* 8, 1-13 (2018).

Pardue, M. T. & Allen, R. S. Neuroprotective strategies for retinal disease. *Prog. Retin. Eye Res.* 65. 50-76 (2018).

Park YR, Yoon YJ, Koo H, Yoo S, Choi CM, Beck SH, Kim TW. Utilization of a Clinical Trial Management System for the Whole Clinical Trial Process as an Integrated Database: System Development. J Med Internet Res. Apr. 24, 2018;20(4):e103. doi: 10.2196/mir.9312. PMID: 29691212; PMCID: PMC5941091.

Pennington, K. L. & DeAngelis, M. M. Epidemiology of age-related macular degeneration (AMD): associations with cardiovascular disease phenotypes and lipid factors. *Eye Vis.* 3, 1-20 (2016).

Russell, S. et al. Efficacy and safety of voretigene neparvovec (AAV2-hRPE65v2) in patients with RPE65-mediated inherited retinal dystrophy: a randomised, controlled, open-label, phase 3 trial. *Lancet* 390, 849-860 (2017).

Scoles, D. et al. In Vivo Imaging of Human Cone Photoreceptor Inner Segments. *Investig. Ophthalmol. Vis. Sci.* 55, 4244-4251 (2014).

Stein, D. M. et al. A new quality assessment parameter for optical coherence tomography. *Br. J. Ophthalmol.* 90, 186 LP-190 (2006).

Sugita, S. et al. Stemming retinal regeneration with pluripotent stem cells. *Prog. Retin. Eye Res.* 0-1 (2018). doi:10.1016/j.preteyeres.2018.11.003.

Takahashi, V. K. L., Takiuti, J. T., Jauregui, R. & Tsang, S. H. Gene therapy in inherited retinal degenerative diseases, a review. *Ophthalmic Genet.* 39, 560-568 (2018).

Talcott, K. E. et al. Longitudinal study of cone photoreceptors during retinal degeneration and in response to ciliary neurotrophic factor treatment. *Investig. Ophthalmol. Vis. Sci.* 52, 2219-2226 (2011).

Wahle et al., "Extending the XNAT archive tool for image and analysis management in ophthalmology research," Proceedings of SPIE, vol. 8674, Mar. 29, 2013, 15 pages.

Notification of Transmittal of the International Search Report and the Written Opinion of the International Searching Authority, or the Declaration, PCT/US2019/049472, Nov. 7, 2019, 18 pages.

* cited by examiner

METHODS, SYSTEMS AND COMPUTER PROGRAM PRODUCTS FOR RETROSPECTIVE DATA MINING

CLAIM OF PRIORITY

The present application is a continuation of U.S. application Ser. No. 17/272,472, filed Mar. 1, 2021, which is a U.S. national phase application under 35 U.S.C. § 371 of International Application No. PCT/US2019/049472, filed Sep. 4, 2019, which claims the benefit of U.S. Provisional Application No. 62/727,072, filed Sep. 5, 2018, entitled Methods, Systems and Computer Program Products for Retrospective Data Mining, the contents of which are hereby incorporated herein by reference in their entireties.

BACKGROUND

Images play an increasingly important role in the diagnosis, treatment, and management of disease. In particular, the way images are used in the diagnosis and management of disease is rapidly evolving. At the most basic level, images are presented to experts for interpretation. Such is often the case with radiograms, sonograms, and photographs. The experts may be, for example, point of care physicians, radiologists, pathologists, and trained technical experts. Increasingly, quantitative analysis is applied to individual images and the quantitative information may be directly interpreted, compared to normative data, or compared to trending data. In such cases, the diagnostic conclusion and impact on treatment remains in the hands of the expert care giver. Big Data and methods of artificial intelligence (AI) are increasingly important to the discovery of diagnostic markers, or imaging biomarkers. The process for developing, validating, and deploying new diagnostic markers for clinical care or as outcome measures in clinical trials for new treatments require an end to end framework for collection, management, and operation on increasingly large volumes of images and data.

SUMMARY

Some embodiments of the present inventive concept provide an integrated system for processing and using images acquired of subjects in a research or clinical environment. The integrated system includes an image and data bank including a plurality of raw images originating from one or more image-generating devices, data associated with the raw images, and data associated with imaged subjects. The system further includes a workflow management module in direct communication with the image and data bank and with the one or more image-generating devices and/or storage devices that store the raw images of the imaged subjects, the workflow management module being configured to transport the raw images directly from the one or more image-generating devices and/or storage devices to the image and data bank and to manage and analyze the raw images, data associated with the raw images and the data associated with the imaged subjects in the image and data bank. A cloud storage module is provided in a cloud configured to store processed images and data from the workflow management module. A pre-processing engine is positioned between the workflow management module and the cloud storage module, the pre-processing engine being configured to receive the raw images, data associated with the raw images and the data associated with the imaged subjects from the workflow management module and process the raw images, data associated with the raw images and the data associated with the imaged subjects to provide the processed images and data before the processed images and data are pushed into the cloud storage module. The cloud storage module is configured to receive the processed images and data from the pre-processing engine. The pre-processing engine is configured to anonymize the raw images, data associated with the raw images and the data associated with the imaged subjects to provide de-identified images and data to the cloud storage module and create a key that relates the raw images, data associated with the raw images and the data associated with the imaged subjects to the de-identified, processed images and data, the key remaining separate and un-connected from the de-identified, processed images and data. The key allows the de-identified, processed images and data to maintain traceability to the imaged subjects and to all subsequent operations on the images and data.

In further embodiments, the pre-processing engine may be further configured to receive the raw images, data associated with the raw images, and data associated with imaged subjects through the workflow management module; determine a specific set of instructions associated with the received raw images, data associated with the raw images, and data associated with imaged subjects from the workflow management module; and process the received raw images, data associated with the raw images, and data associated with imaged subjects based on the specific set of instructions associated with the received raw images and data from the workflow management module to provide the de-identified, processed images and data.

In still further embodiments, the specific set of instructions associated with the received raw images, data associated with the raw images, and data associated with imaged subjects may be determined by an indicator set in a data field, the indicator directing the pre-processing engine to the specific set of instructions for the received raw images, data associated with the raw images, and data associated with imaged subjects from a particular device.

In some embodiments, the pre-processing engine may be further configured to at least one of validate, quantify, annotate and classify the raw images, data associated with the raw images, and data associated with imaged subjects received from the workflow management module.

In further embodiments, the pre-processing engine may be configured to remove non-essential or private data from the raw images, data associated with the raw images, and data associated with imaged subjects; store the removed non-essential or private data; and before recycling the non-essential or private data, request permission from a user associated with the raw images and data.

In still further embodiments, the workflow management module may store the raw images, data associated with the raw images, and data associated with imaged subjects in a structured manner using a relational or structured query language (SQL) database and the cloud storage module may store the de-identified, processed images and data in an unstructured manner using a non-relational or Non-SQL database.

In some embodiments, the system may further include at least one of the following modules in the cloud: an algorithm module in communication with the cloud storage module, the algorithm module configured to apply a set of rules to at least a portion of the de-identified, processed images and data stored in the cloud storage module; a recipe module in communicate with the cloud storage module, the recipe module configured to apply a series of algorithms to at least a portion of de-identified, processed images and data stored in the cloud storage module; and a derivation module in communication with the cloud storage module, the derivation module configured to use at least a portion of the de-identified, processed images and data stored in the cloud storage module and derive new images and data therefrom.

In further embodiments, the derivation module may be configured to assess quality of the de-identified, processed images and data; reduce noise in de-identified, processed images and data; segment the images and data; and/or measure de-identified, processed images and data.

In still further embodiments, the de-identified, processed images and data stored in the cloud storage module may be automatically updated by various modules in the cloud.

In some embodiments, the modules in the cloud may utilize one or more of artificial intelligence (AI), statistical abstraction; image abstraction and image extraction.

In further embodiments, the de-identified, processed images and data stored in the cloud storage module may include at least one of statistical data; processed images; reduced images; retrospective images; in vivo images; in vitro images; functional test results; and biospecimen test results.

In still further embodiments, transactions and operations applied to the raw images, data associated with the raw images, and data associated with imaged subjects and to subsequent processed images and data resulting from the transactions and operations may be recorded in a block-chain-like ledger.

In some embodiments, the transactions and operations recorded in the ledger may include allocation of subsets of images and data used for training, testing, and validation operations.

In further embodiments, the image and data bank may include ophthalmic images and data.

In still further embodiments, the integrated system may provide a system for collecting, managing and mining images and data that are periodically updated and refined and using the images and data together with any derived data for training, testing, and validation of algorithms for development of one or more of markers of disease and disease progress, markers of physiological response to internal and external factors including therapeutic interventions, correlation of phenotypes with genotypes, and development of diagnostic and prognostic measurements and methodologies.

Some embodiments of the present inventive concept provide related methods and computer program products.

DETAILED DESCRIPTION OF EMBODIMENTS

Figure 1:
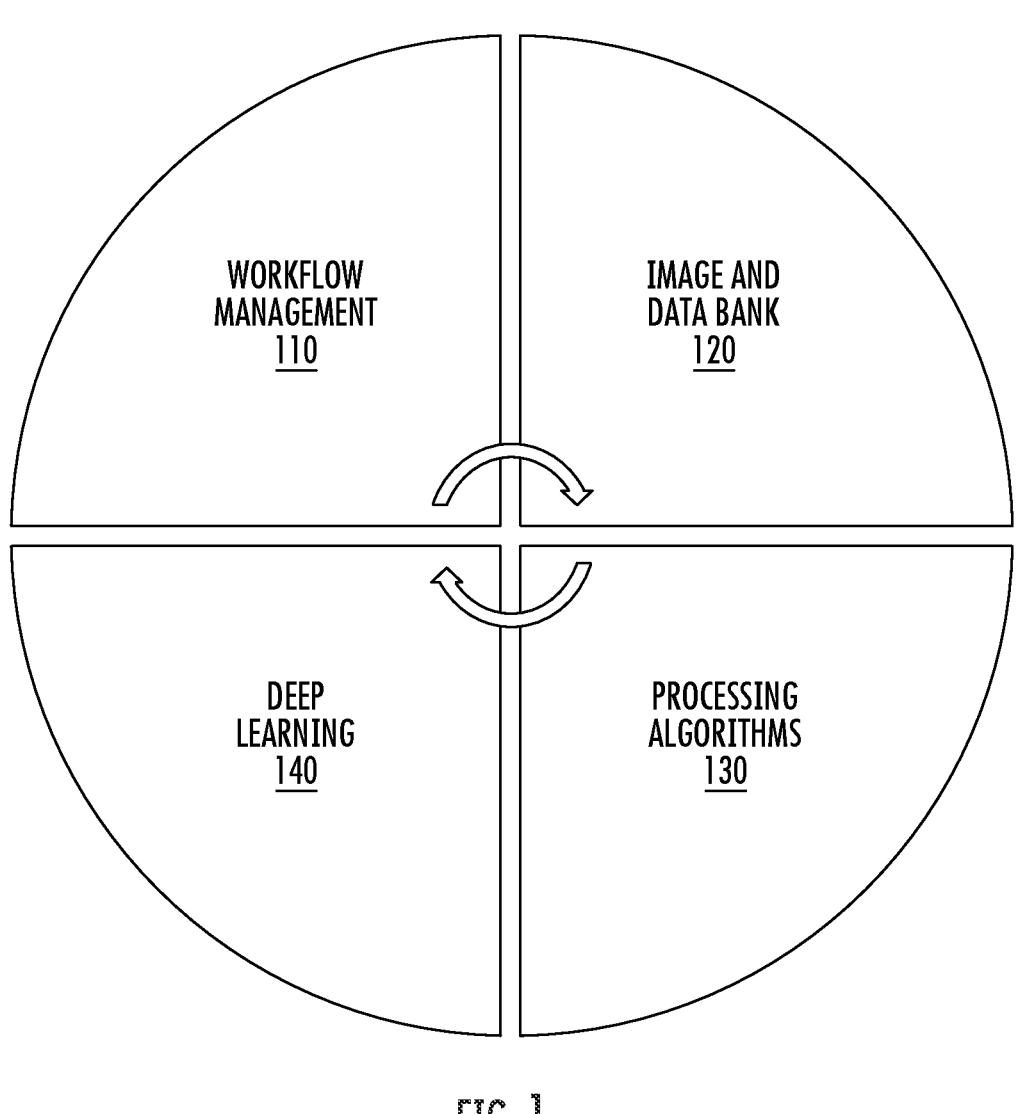
FIG. 1 is diagram illustrating components of deep learning system in accordance with some embodiments of the present inventive concept.

The inventive concept now will be described more fully hereinafter with reference to the accompanying drawings, in which illustrative embodiments of the inventive concept are shown. This inventive concept may, however, be embodied in many different forms and should not be construed as limited to the embodiments set forth herein; rather, these embodiments are provided so that this disclosure will be thorough and complete, and will fully convey the scope of the inventive concept to those skilled in the art. Like numbers refer to like elements throughout. As used herein, the term "and/or" includes any and all combinations of one or more of the associated listed items.

The terminology used herein is for the purpose of describing particular embodiments only and is not intended to be limiting of the inventive concept. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this inventive concept belongs. It will be further understood that terms, such as those defined in commonly used dictionaries, should be interpreted as having a meaning that is consistent with their meaning in the context of the relevant art and this specification and will not be interpreted in an idealized or overly formal sense unless expressly so defined herein.

As will be appreciated by one of skill in the art, the inventive concept may be embodied as a method, data processing system, or computer program product. Accordingly, the present inventive concept may take the form of an entirely hardware embodiment or an embodiment combining software and hardware aspects all generally referred to herein as a "circuit" or "module." Furthermore, the present inventive concept may take the form of a computer program product on a computer-usable storage medium having computer-usable program code embodied in the medium. Any suitable computer readable medium may be utilized including hard disks, CD-ROMs, optical storage devices, a transmission media such as those supporting the Internet or an intranet, or magnetic storage devices.

Computer program code for carrying out operations of the present inventive concept may be written in an object-oriented programming language such as Java®, Smalltalk or C++. However, the computer program code for carrying out operations of the present inventive concept may also be written in conventional procedural programming languages, such as the "C" programming language or in a visually oriented programming environment, such as VisualBasic.

The program code may execute entirely on the user's computer, partly on the user's computer, as a stand-alone software package, partly on the user's computer and partly on a remote computer or entirely on the remote computer. In the latter scenario, the remote computer may be connected to the user's computer through a local area network (LAN) or a wide area network (WAN), or the connection may be made to an external computer (for example, through the Internet using an Internet Service Provider).

The inventive concept is described in part below with reference to a flowchart illustration and/or block diagrams of methods, systems and computer program products according to embodiments of the inventive concept. It will be understood that each block of the illustrations, and combinations of blocks, can be implemented by computer program instructions. These computer program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the block or blocks.

These computer program instructions may also be stored in a computer-readable memory that can direct a computer or other programmable data processing apparatus to function in a particular manner, such that the instructions stored in the computer-readable memory produce an article of manufacture including instruction means which implement the function/act specified in the block or blocks.

The computer program instructions may also be loaded onto a computer or other programmable data processing apparatus to cause a series of operational steps to be performed on the computer or other programmable apparatus to produce a computer implemented process such that the instructions which execute on the computer or other programmable apparatus provide steps for implementing the functions/acts specified in the block or blocks.

As discussed in the background, images play an increasingly important role in the diagnosis and management of disease. With the advent of artificial intelligence (AI), machine learning and deep learning techniques, it is becoming viable to enrich the diagnostic content of images by training images against expertly graded examples. For example, a product that uses fundus photographs (photographs of the retina) to provide an automated diagnosis of diabetic retinopathy had been developed and approved by the Federal Drug Administration (FDA). This diagnosis application, which is based on images, highlights both the promise and the limitations of approaches to deep learning. First, the accuracy of the diagnosis is generally less than ninety percent and relegated to patients with intermediate to advanced grades of diabetic retinopathy. While an important contribution to the diagnostic regime, the technology is not ready for early prediction of disease or disease progression. Furthermore, the regulatory clearance related to this product is limited to images acquired using one model of one fundus camera from one manufacturer. So, while this application of deep learning is a sign of the future of AI in image-based medical diagnostics, improvements are desired.

The technology industry is providing very advanced systems and solutions to provide users access to cloud storage and computing facilities and to computational systems for deep learning. For example, cloud-based services are provided by Google, Amazon, Microsoft, IBM and the like. These services are making a rapid impact on the development of deep learning technologies across a variety of applications including medical applications.

Research and proofs of concept for deep learning useful, but the target is translation of research to the clinic.

This generally requires moving algorithms through rigorous regulatory processes. FDA is demonstrating intention to support such digital advances. In order to successfully navigate the regulatory landscape, it remains essential to follow a structured, reproducible and validated design control process and to provide clear evidence for the verification and validation of digital medical solutions. This process starts early, with clear definition of the intended use for a new medical device, including a digital medical device, deriving requirements for the performance and deployment of the device consistent with the intended use, translating market requirements to technical specifications, developing the device, freezing developing, and completing verification and validation according the requirements and the intended use, respectively.

Critically, the verification and validation steps must be traceable to the requirements. In prognostic and diagnostic devices derived from medical images, the workflow for shepherding a new product through successful regulatory clearance is a very complex and cumbersome process involving the development of clinical trial protocols, management of patient consents and patient privacy, scheduling patients, and following formal protocols in the collection, storage and management of image data and associated metadata. In order to develop the diagnostic indicators, biomarkers, or endpoints, the research team will need to iterate through a number of steps.

Accordingly, some embodiments of the present inventive concept use a central application as a platform for prospective and retrospective image based biomedical research, in addition to an image bank of millions of images and image processing algorithms to increase the efficiency of imaging-driven biomedical research and clinical trials through structured workflow management; build and manage a de-identified image bank as a platform for the sharing and re-use of expensive research and clinical images; provide a platform for both the prospective and biomarkers, endpoints, and clinical trial outcome measures; provide a platform for third-party development of algorithms for image processing and deep learning; and increase the efficacy of translating these activities to the clinic and market by structuring these activities in a rigorous, transparent, reproducible and validated process.

LATTICE is an Electronic Research Record developed at the Medical College of Wisconsin to increase the efficiency of translational research in vision and ophthalmology. As implemented, the software has specific utility to retinal imaging. As an architecture, it is a flexible Software as a service (SaaS) platform for living-subjects image and data based translational research. LATTICE and its related functionality are used in embodiments of the present inventive concept and, therefore, these teachings are incorporated herein by reference as if set forth in their entirety.

LATTICE is a software system for managing the scheduling of subjects, tracking of subjects during research encounters, and collection of clinical images for running efficient prospective clinical trials in ophthalmology. This platform has significant potential for commercialization, as the trends in ophthalmology and translational medicine strongly favor efficiency in clinical trials, maximum re-use and sharing of images collected under federal grants, and rapid advancement of deep learning technologies that require banks of PHI protected images to train and validate new diagnostic algorithms.

As discussed above and illustrated in FIG. 1, embodiments of the present inventive concept combine a workflow management system 110, for example, LATTICE; an image database 120, for example, a library of approximately 3,000,000 retinal images; and processing algorithms 130, for example, as deployed within MOSAIC, which houses intelligent image quantification algorithms, developed with deep learning principals (AI) 140 to provide a commercial platform for managing image-based clinical trials, maximizing licensed re-use of images for retrospective studies, and developing learning algorithms for advancing clinical diagnostics.

In will be understood that although, LATTICE, MOSAIC and a specific database of retinal images are specifically discussed herein, embodiments of the present inventive concept are not limited to this configuration. For example, any workflow management system, image bank or processing algorithms may be used to provide the results as discussed herein without departing from the scope of the present inventive concept.

As used herein, an image bank can include any collection of images as needed for embodiments of the present inventive concept. For example, an image bank may include a collection of optical coherence tomography (OCT), OCTA photographic, and adaptive-optic images and associated metadata, collected under internal ratings-based (IRB) approval with informed consent allowing image re-use. As used herein, "metadata" refers to, but is not limited to, any patient demographics, medical histories, diagnoses that inform the images, subject to any and all protections under applicable United States and international patient privacy regulations.

As will be discussed further herein, embodiments of the present inventive concept use the workflow management system (LATTICE) and image and data bank to create a unified platform for the collection, mining, sharing, and exploration of pre-clinical and clinical image data. The objective is to create a "Design Control" system for image-based research that maximizes the translation of research insights and new diagnostic modalities to the market to advance ocular healthcare and reduce healthcare costs.

Users of this product may include academic researchers, researchers in the biotech and pharma space developing new therapies, contract research organizations (CROs) running clinical trials on behalf of industrial partners, as well as the big data firms that are seeking to sell cloud services and establish their own footprint in healthcare. Embodiments of the present inventive concept may be configured to link to web tools for researchers to accelerate their own algorithm development, training, and testing.

Figure 2:
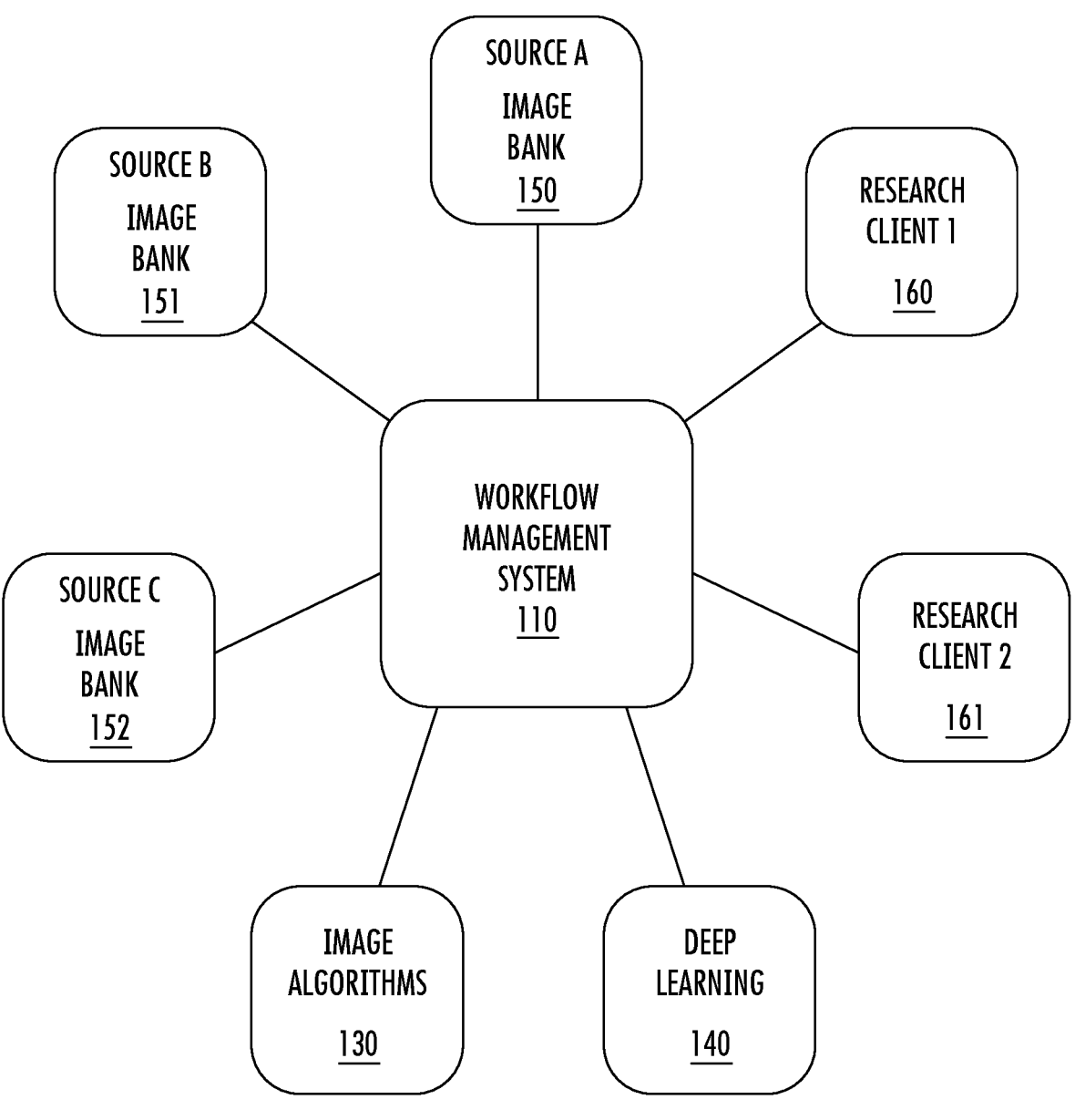
FIG. 2 is a block diagram of an integrated system in accordance with some embodiments of the present inventive concept.

The fully integrated platform in accordance with embodiments discussed herein will further be discussed with respect to FIG. 2. As illustrated therein, the platform includes a workflow management solution 110, for example, LATTICE, for collecting, managing and mining image-based research and clinical data. In some embodiments, subscription services for use of LATTICE may be provided. Some embodiments of the present inventive concept may expand image-centric fields beyond ophthalmology without departing from the scope of the present inventive concept. In other words, image banks including any type of image may be used in accordance with embodiments discussed herein. As illustrated FIG. 2, the workflow management function 110 couples multiple image banks, Source A 150, Source B 151 and Source C 152, multiple research clients 161 and 162, processing algorithms 130, for example, MOSAIC, and deep learning modules 140 to provide the integrated system.

In some embodiments, the image bank 120, 150, 151 and 152 may include a collection of approximately 3,000,000 images collected over a decade of research, or any other quantity of images collected over any period of time. As illustrated in FIG. 2, the workflow management system 110 (LATTICE) has access to more than one image bank, Source A 150, Source B 151 and Source C 152. In some embodiments, the image bank may be curated, categorized, anonymized, and validated for sharing and re-use with evidence of provenance, IRB approval, and patient consents that authorize retrospective use of images under defined circumstances.

Figure 3:
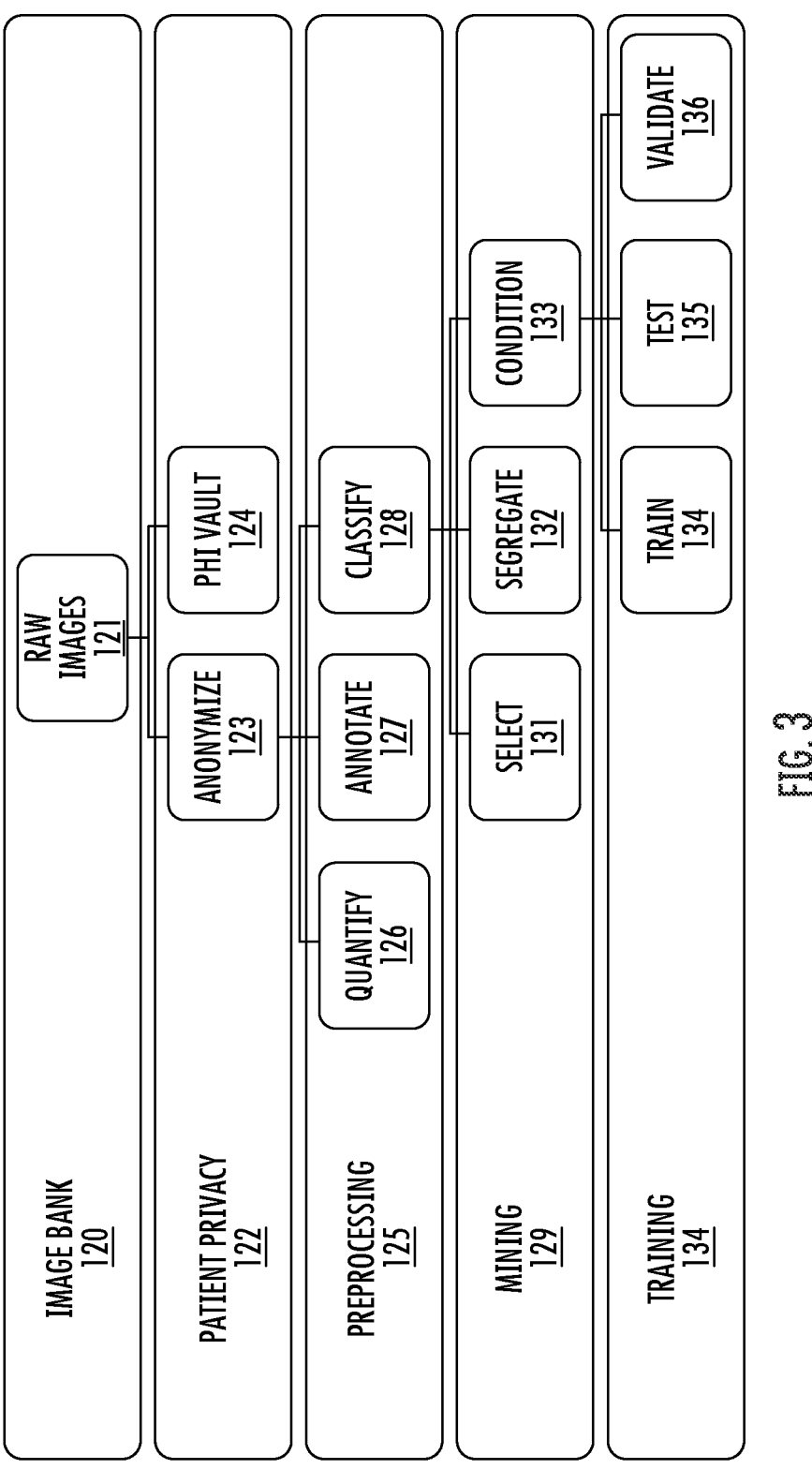
FIG. 3 is a diagram illustrating various categories of data according to some embodiments of the present inventive concept.

Referring now to FIG. 3, a diagram illustrating various categories of data according to some embodiments of the present inventive concept will be discussed. As illustrated, an image bank may include raw images 121, which may be processed to provide images compliant with patient privacy standards 122 (anonymize 123, Patient Health Information (PHI) vault 124); pre-processed 125 to allow annotation and the like (quantify 126, annotate 127 and classify 128); mined 129 to find specific images meeting specific criteria (select 131, segregate 132 and condition 133); and used in training 134, testing 135 and validation 136.

Providing the various processed images as discussed with respect to FIG. 3 may add value to the services. For example, pre-processing 125 the images may include manual, automated, or semi-automated marking, segmentation, and quantification 126. This may include layer segmentation, cell counting (as with MOSAIC) or other marking that reduce the raw image to a derived data set suitable for further analysis. Medical annotation 127 may involve the addition of expert opinion to the image, identifying pathology or disease, or grading disease according to standards. Classification 128 may involve establishing a schema for categorizing images for mining and retrospective analysis. In each case, the original raw images and data are preserved, and actions taken with respect to the images and data are recorded as transactions, and the results from transactions are stored as derived results that link back to the raw images and data and the processing transactions.

Some embodiments of the present inventive concept are provided for use in deep learning studies (AI). In these embodiments, images drawn from the image bank 120 may be further segregated into randomized independent sets for training 134, testing 135 and validation 136 of algorithms as illustrated in FIG. 3. In order to increase the robustness of deep learning algorithms, training images 134 may be further conditioned to added representative real-world variability to the images. The more the workflow can be standardized and reproduced, the more efficient the study. Additionally, the more standardized and reproducible the workflow, the easier to generate credible, reproducible results and the faster the regulatory clearance process for resultant clinical solutions.

MOSAIC houses a specific algorithm for analyzing photoreceptors in adaptive optic enhanced fundus images. Adaptive optic (AO) imaging systems are not yet a standard of care in ophthalmology but are used in research and clinical trials. Broadening the analysis of AO images through MOSAIC in accordance with embodiments of the present inventive concept may help to identify clinical endpoints that can drive adoption of adaptive optics and address open clinical questions related to inherited retinal disease and age-related degenerative disease. In some embodiments, MOSAIC may be appropriately applied to images in the image bank 120 to provide a reduced data set (locations and count of photoreceptors) for further analysis. Alternatively, MOSAIC may be applied to the image bank

120 to provide an annotation to the images as part of the ontology for categorizing images as will be discussed further herein.

Figure 4:
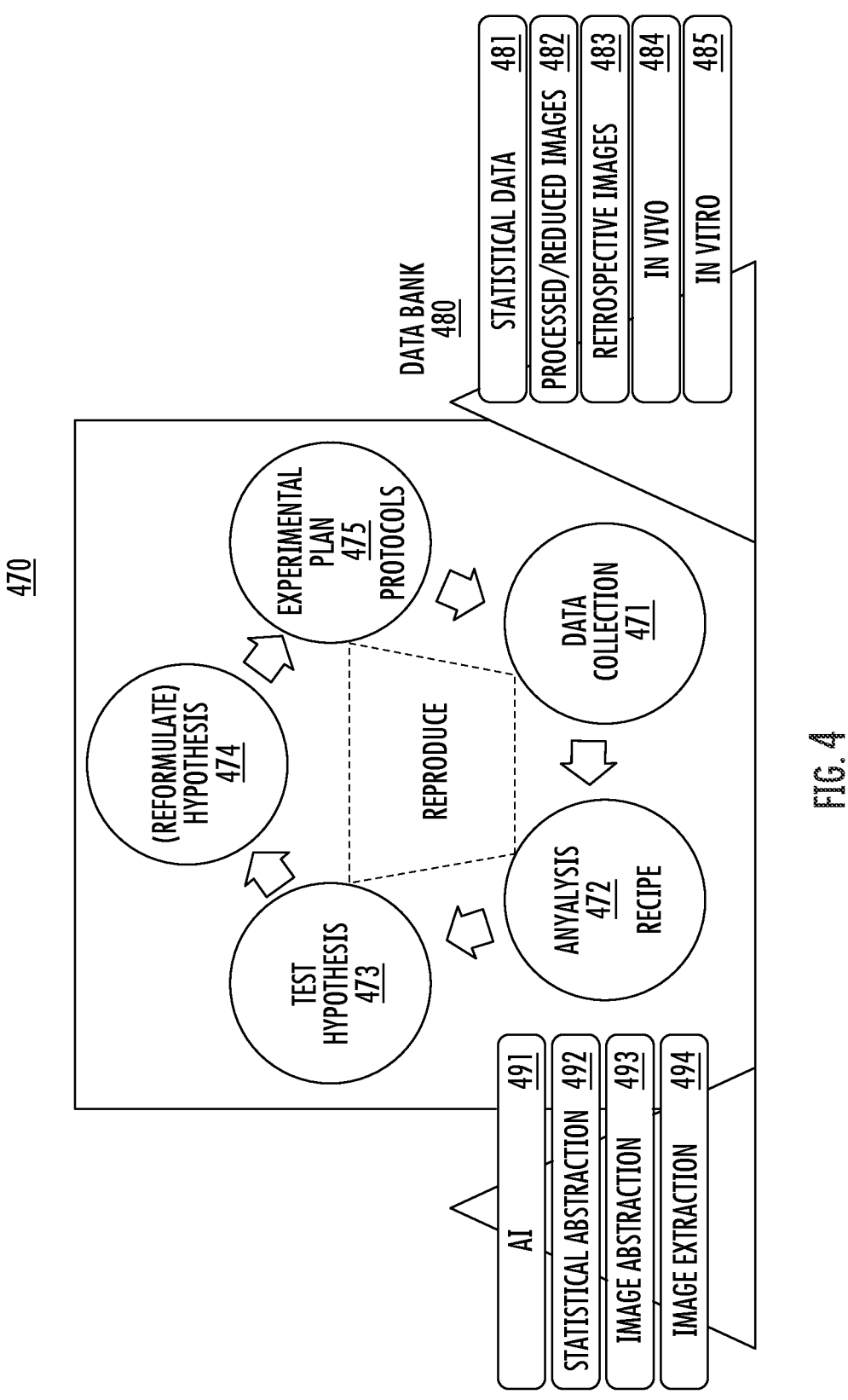
FIGS. 4 and 5 are diagrams of data flows in accordance with some embodiments of the present inventive concept.

As discussed above, embodiments of the present inventive concept provide an integrated system for multiple uses, for example, training, testing, validation, and diagnosis. FIG. 4 is a diagram illustrating the data flow in a test environment of how data is collected, analyzed and used to create and reformulate hypotheses in accordance with some embodiments of the present inventive concept. As illustrated in FIG. 4, the workflow 470 collects data 471 from the data bank 480 including, for example, statistical data 481, processed/reduced images 482, retrospective images 483, in vivo data 484, in vitro data 485 and the like. This data may be analyzed 472 using recipes. Analyzing 472 the data 480 may include deep learning 490 including AI 491, statistical abstraction 492, image abstraction 493, image extraction 493 and the like. Using this analysis, a hypothesis 473 may be generated, tested and reformulated 474. From this an experimental plan 475 may be created using protocols and the like. As illustrated by the arrows in FIG. 4, these steps may be repeated over and over to constantly refine and redefine the results. Further and unique to embodiments of the present inventive concept, each step maintains complete traceability. In other words, from any step, the starting point (original image and/or data) may be found, thereby maintaining providence of each piece of data-backwards and forwards.

As used herein, the term "recipes" refers to the various algorithms that may be applied to the raw data to provide new sets of data. For example, one "recipe" may be used to anonymize the data, i.e., remove all metadata that points to the patient from which the data refers. Other recipes may involve image processing, statistics and the like. Recipes may be user customizable and there are no limits to the number of recipes that can be created.

Figure 5:
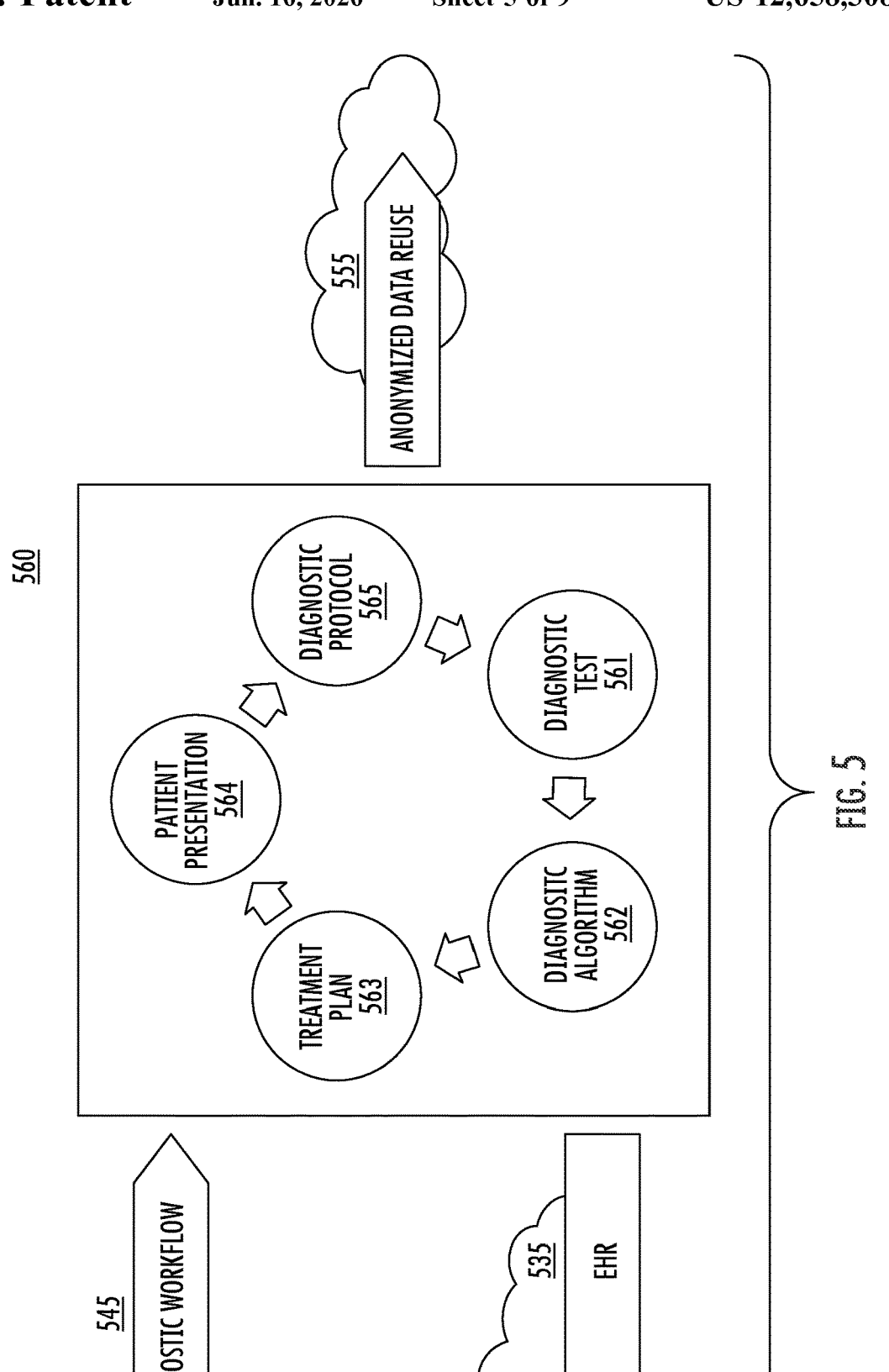

Referring now to FIG. 5, a block diagram illustrating a diagnostic workflow for a patient diagnosis will now be discussed. As illustrated, the diagnostic workflow 560 includes a diagnostic test module 561 which provides the initial data with respect to the patient. This data is submitted to the diagnostic algorithm 562. As discussed above, this algorithm may have access to historical data in a data bank in any form as well as various deep learning modules or other algorithmic recipes. The data may also be stored in an electronic health record (EHR) 535 or anonymized and stored for reuse 555 as discussed herein. Once the data has been run through the diagnostic algorithms 562, a treatment plan 563 may be created. Details of the patient's response to the treatment 564 may be observed and the diagnostic protocol 565 may be revised accordingly. As discussed above with respect to FIG. 4, the process may be repeated over and over to refine the results until a specialized treatment plan that patient responds to is found. As further discussed above, each of these steps can be traced, both forward and backward without departing from the scope of the present inventive concept.

Figure 6:
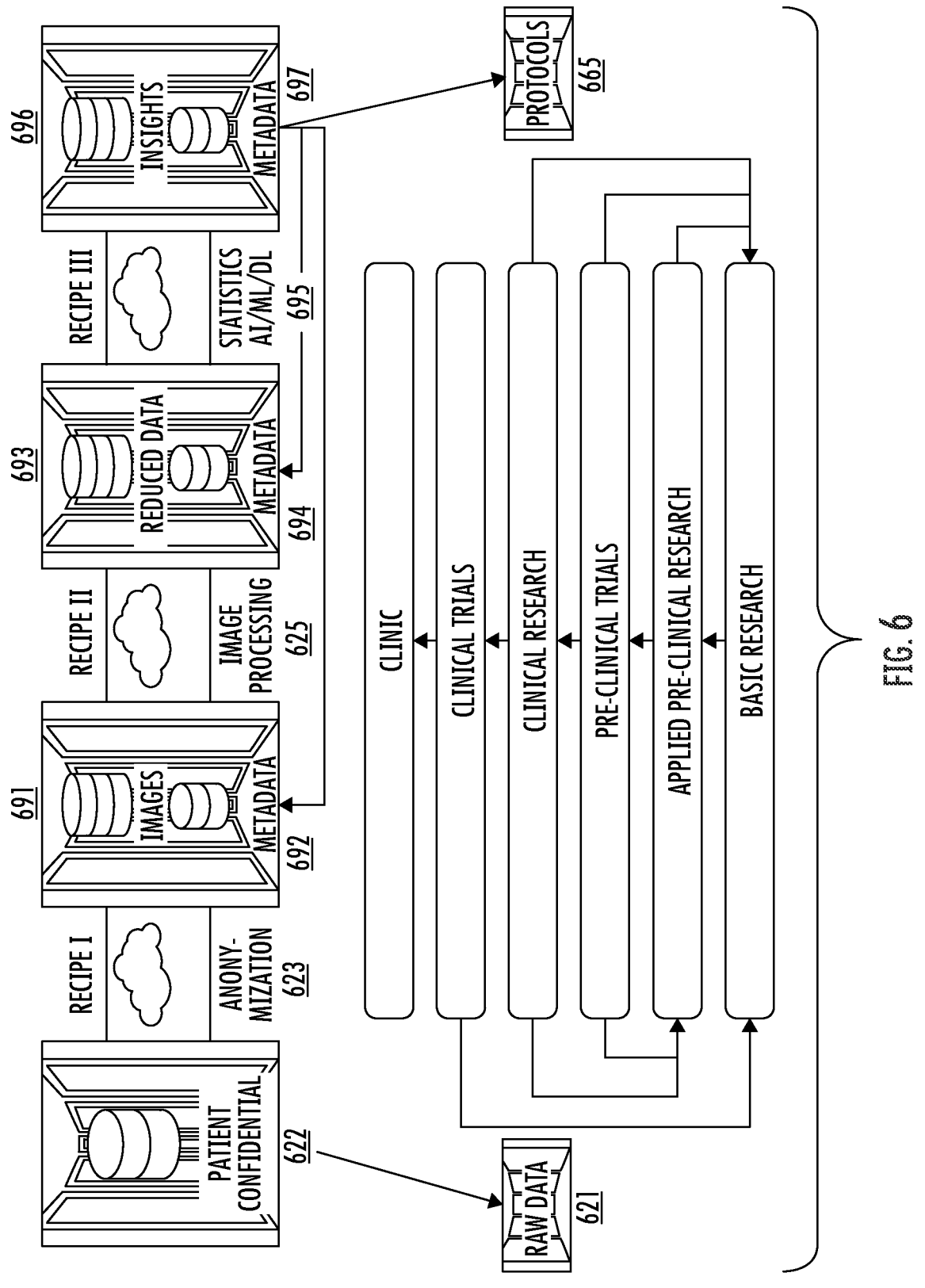
FIG. 6 is a diagram of the integrated system in accordance with some embodiments of the present inventive concept.

FIG. 6 is a block diagram illustrating the integrated system in accordance with embodiments of the present inventive concept. As discussed above, embodiments of the present inventive concept use an image database and this image database may be a database of raw images 621. These raw images 621 may include patient confidential information 622 and metadata. Embodiments of the present inventive concept provide various engines to apply "recipes" to process the data so the data can be used for different applications. For example, an anonymization engine 623 may be apply "recipe I" to remove all the "private" patient data. This anonymized data may split the raw data 621 into images 690 into metadata 692, the two data sets connected by a confidential key. At this point, the image may be further processed by various engines, classification engine, mining engine, training engine, test engine, and validation engine. These various engines can process the data in a series of sequential steps and store derived results in a form traceable to the original data and to additional introduced data, and to the processing engines or rules, useful for the various purposes, and transparent with respect to order of events. For example, the images may be annotated with comments from experts such as doctors and researchers. For example, an expert may annotate an image with a diagnosis, such as glaucoma. The images may also be shifted, rotated, denoised and the like and such derived data may be stored with the perturbations, preferably as new copies such that the provenance of original images and data is fully preserved. As further illustrated, "recipe II" may be an image processing 625 recipe and may provide a reduced image 693 and additional metadata 694. An example of the reduced image may be a segmentation map fully correlated to the original image but without the pixel values of the original image. "Recipe III" may be a statistical recipe 695 applying deep learning and providing insights 696 and additional metadata 697. The metadata provided at each step allows the algorithm to retrace its steps all the way back to the raw image 621. All of this data may be used to create and refine protocols 665. The data may be used in clinics, clinical trials, clinical research, pre-clinical trials, applied pre-clinical trials, basic research and the like.

Thus, data is accumulated, classified, anonymized, extracted and annotated and stored after the particular engine has performed its function. Once stored the images may be made available to the various users in a database(s). The images may be stored having various privacy levels, from public and open to proprietary, private, and closed. The private data may be stored behind an interface requiring a key for entry.

As discussed above, the images may be prepared and studied. The database of images may be mined (queried) based on many factors including classification. The classified data may be segregated into sets according to various rules and the rules may change over time. Thus, the algorithms learn over time. For example, as data privacy laws change, so will the rules ("recipe") applied to the data when the data is being processed. The various data sets may be used to train/teach, verify test and validate. The validation set may preferable be segregated from the training and tests sets in order to confirm that the algorithm or recipe being validated has not been biased or contaminated by previous access to the validation data set. The algorithms or recipes are only validated when all tests have been met when tested on data that has not been previously used during training and testing. The data may be stored in a database accessible to the cloud so that the data may be used by others on the cloud.

In order to provide traceability to the large number of transactions, algorithms and recipes that may be applied to an image data set for the purposes of biomarker or diagnostic development, validation, regulatory clearance, and deployment, a clear, traceable record of all interactions with and operations on the data must be maintained. Additionally, living-subjects' data generally requires security, respect of patient privacy rights, and agreements of limitations of use, disclosure, and financial transactions that involve the data directly or involve insights derived from the data. A record of all user interactions and use of the data must be maintained with consideration of the contracts that govern legitimate use of the data. These objectives point to two separate, if related, uses for ledgers to record histories of user access to data, and to record the processes of operations applied to data for the purposes of validating the discovery and development of new insights, diagnostics, and biomarkers and the like from the data. Blockchain ledgers are thus useful for recording data contracts and access, and for tracing operations on data during algorithm and recipe development and validation.

In particular, the blockchain is a growing list of records, called block, which are linked using cryptography. Each block contains a cryptographic hash of the previous block, a timestamp, and transaction data. In other words, the blockchain is a system of distributed ledgers used to store records of transactions. Think of it as a database, but instead of storing a single version of the database on one computer or server, everyone involved in the blockchain has their own copy of the same ledger. The blockchain is so named because it consists of a series of "blocks." As transactions are completed, new blocks are added to the chain. Thus, is someone wants to change something in the blockchain, all (or mostly all) the ledgers must agree before the change can be made. Thus, storage in the blockchain is secure and hard the security is difficult to breach. Blockchain structures in the context of the proposed workflow, image management, and image processing platform are thus particularly useful in distributed, multi-site environments that are the norm in clinical research and development.

Referring again to FIG. 6, embodiments of the present inventive concept may allow the image data to be accessible in various forms to various users, for example, clinic, clinical trials, clinical research, pre-clinical trial, applied pre-clinical research, basic research and the like. Providing the various engines to process the data before it is stored allows the data to be provided in a usable format for each user without violating privacy laws.

Some embodiments of the present inventive concept provide an image management system for the development and validation of diagnostic endpoints. In some embodiments, the system includes static database containing static records for individual images. The records may include a reference code that is unique to the image and distinct from patient identifying information; a series of fields that define the equipment from which the image was acquired; a series of fields that define the site at which the image was acquired; a series of fields that define the demographics of the subject of the image; and a series of fields that define known subject condition attributes.

In further embodiments, a database containing dynamic records for individual images may be provided. The record may include a history of the access to the image, a history of algorithms applied to the image for the purpose of deriving a reduced set of data from the image; the existence and location of a reduced set of data derived from the image; a history of annotations applied to the image for the purpose of applying an expert comment to the image; and the existence and location of the expert comment applied to the image;

Still further embodiments provide a processing engine to validate the de-identification and protection of subject privacy. The privacy engine includes a set of rules applied against the static or dynamic database records that test for the presence of subject identifiable content and that applies a flag to the image, the static database, or the dynamic database that indicates the presence of lack of subject identifying content.

Some embodiments provide a processing engine to select from and apply one or more algorithms to modify an image according to a set of algorithmic objectives, to derive a reduced set of data unique to the image, or extract derived attributes from images, and to store the algorithmic steps, the modified image, the reduced data set, or the derived attributes for recall without modifying the original image.

Further embodiments of the present inventive concept provide an engine to provide selected images engines, original or images as modified by the Image Pre-processing Engine, to a subject matter expert and to collect annotations provided by the subject matter expert. The annotations become a record within the static or dynamic database.

Still further embodiments of the present inventive concept provide a processing engine to classify and index one or more images against a multiplicity of fields from one or more of the databases, including based on annotations developed through pre-processing in the expert annotation engine. The classification describes commonality of attributes against which future subjects are tested.

Some embodiments provide a randomization engine to select a multiplicity of images according a classification, select images according to a randomization algorithm, flag each of the multiplicity of randomized images uniquely into one of three or more sets. One set of images is used for training of an automated image processing algorithm, one set of images is used for testing the trained algorithm, and one set of images is used to validate the trained algorithm.

Various populations may be defined. For example, population 1 (optional) is a population of normal or controls; population 2 (required) is a training population of subjects in like classification and in unlike populations used to develop algorithm for including future subjects into classification; population 3 (required) is test population of subjects in like classification and in unlike populations used to test algorithm during development for including future subjects into classification; and population 4 (required) is a validation population; blind population of subjects that are graded to be within or without the target classification, against which the final trained algorithm may be tested for accuracy (sensitivity and specificity) using known methods of analysis. In some embodiments, the platform automates the segregation of available data into these various populations using random assignment, with the support of user-defined proportions of data to be set aside into the various populations. The use of the data is then traced and recorded, for example, in the blockchain ledger of transactions and operations.

Still further embodiments provide an interactive pre-processing engine that operates on a training population set aggregated from the Deep Learning randomization engine, to perform one or a multiplicity of steps to establish features, or attributes from an original image, a modified image, or a derived data set from images that are indicative of a classification that is to be automated by the Deep Learning engine.

Some embodiments provide a batch processing engine that applies a recipe consisting of one more algorithms applied in parallel, sequentially, or in combination to at least one set of images that are a full set of images chosen from by the randomization engine or a subset of such a set.

Further embodiments provide a processing engine to create an automated image classification algorithm that operates on images using a series of pre-processing steps defined by the processing engines of the subject system, to classify images in a manner that matches the classification scheme defined in the system and is validated or validatable by subject matter experts substantially equivalently to annotation of the training image set.

Still further embodiments provide a decision engine that provides a binary output stating that a classification test returns a positive or negative result with respect to the target classification.

Some embodiments provide a visualization engine that displays one or images, an indication of the classification of the image as drawn from the static or dynamic database, and a result of the algorithm or recipe.

Further embodiments of the present inventive concept provide a statistical test engine that performs one or more statistical tests of the result of a recipe or algorithm applied to a set or subset of images.

Still further embodiments provide a workflow recording engine that maintains and records a series of operations used from among the processes of de-identification, classification, randomization, batch processing, decision making, visualization, and statistical testing.

Some embodiments provide a workflow editing engine that presents a visual representation of the ordered set of the recorded workflow steps as a list or as a set of graphical elements that may be edited, truncated, added to, or reordered to create a different workflow. Editing may include different steps or select different data, or apply different algorithms, or apply different statistical tests or the like.

Further embodiments provide a workflow replication engine that reruns an original or edited workflow on a previous, modified, or new data set.

Still further embodiments provide a validation accumulation engine that runs a previous workflow on a new data set and combines the results into a new statistical test that includes in its population a previous data set and the new data set.

Figure 7:
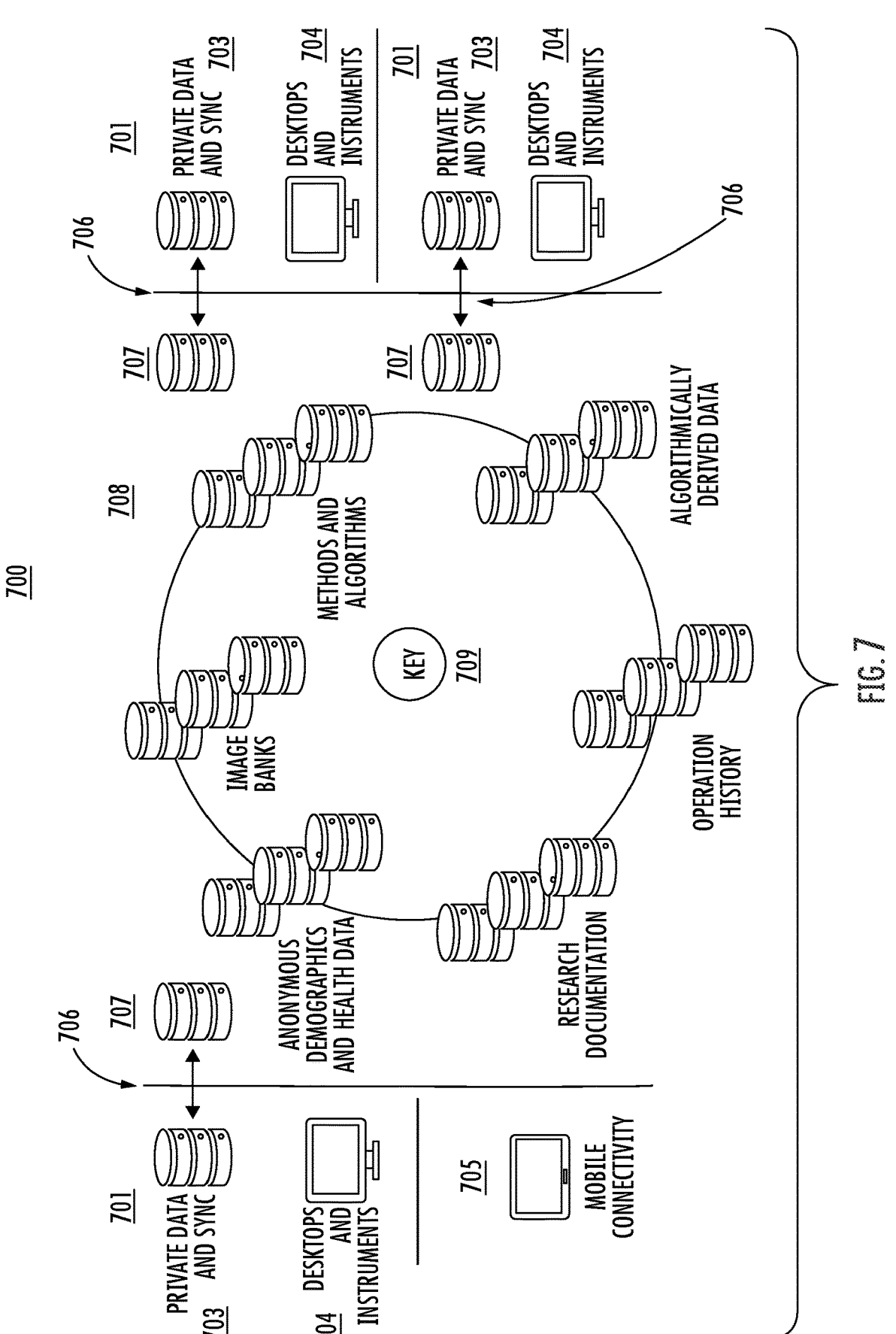
FIG. 7 is a block diagram of an integrated system in accordance with some embodiments of the present inventive concept.

Referring now to FIG. 7, an example embodiment of an integrated system for processing and using images acquired of subjects in a research or clinical environment in accordance with some embodiments of the present inventive concept will now be discussed. Although FIG. 7 illustrates a system including various modules/devices inside and outside the cloud, embodiments of the present inventive concept are not limited to this configuration. For example, there may be more or less than three private data sources without departing from the scope of the present inventive concept.

As illustrated in FIG. 7, the system 700 includes a plurality of private systems 701 including communications equipment 704 and private data storage 703; a mobile connectivity module 705, a plurality of pre-processing engines 706 between the private systems and a cloud storage module 707 and various modules (algorithms, derived data, historical data, reach documentation, de-identified data and the like) and data storage (anonymous data and image banks) in the cloud 708. As discussed above, the system 700 illustrated in FIG. 7 is provided for example only and should not limited embodiments of the present inventive concept. It will be further understood that the information discussed with respect to the system 700 could be stored in a blockchain environment and used accordingly.

Referring to FIG. 7, the plurality of private systems 701 include private data stored in an image and data bank 703. This data and the associated images are generally raw data that includes information (metadata) that indicates the source of the data when the data was collected and the like. In other words, the image and data bank may include, for example, raw images originating from one or more image-generating devices and/or storage devices, data associated with the raw images, and data associated with imaged subjects. The image-generating device may be any device known to those of skill in the art without departing from the scope of the present inventive concept. The private data 703 is associated with a workflow management module, for example, LATTICE, which is configured to configured to transport the raw images directly from the one or more image-generating devices and/or storage devices to the image and data bank and to manage and analyze the raw images, data associated with the raw images and the data associated with the imaged subjects in the image and data bank. In embodiments utilizing LATTICE, the functionality thereof is known and, therefore, the details of the LATTICE module will be discussed further herein.

As further illustrated in FIG. 7, a pre-processing engine 706 is positioned between the workflow management module in the private system and a cloud storage module 707. The pre-processing engine 706 is configured to receive the raw images, data associated with the raw images and the data associated with the imaged subjects from the workflow management module and process the raw images, data associated with the raw images and the data associated with the imaged subjects to provide the processed images and data before the processed images and data are pushed into the cloud storage module 707. The cloud storage module 707 is configured to store the processed images and data from the workflow management module.

In some embodiments of the present inventive concept, at a minimum, the pre-processing engine 706 anonymizes (de-identifies) the raw images, data associated with the raw images and the data associated with the imaged subjects to provide de-identified images and data to the cloud storage module 707 and create a key 709 that relates the raw images, data associated with the raw images and the data associated with the imaged subjects to the de-identified, processed images and data. The key 709 remains separate and unconnected from the de-identified, processed images and data in the cloud storage module 707. The key 709 allows the de-identified, processed images and data to maintain traceability to the imaged subjects and to all subsequent operations on the images and data.

In other words, in operation, the various private systems 701 (or sites) use a workflow management system (e.g., LATTICE) to push data into the cloud. However, embodiments of the present inventive concept provide a pre-processing engine 706 between the workflow management system in the private system 701 to de-identify data (anonymize) the data before it is provided to the cloud storage system 707. The data stored at private system/workflow management system is structured, for example, in folders and subfolders. This data may be stored in a relational or structured query language (SQL). The data pushed into the cloud may be stored using unstructured data methods (NOSQL, MongoDB, Cassandra, and the like) in the cloud storage module 707. Each specific imaging or data acquisition device may have a unique application protocol interface (API) that communicates between the device and the workflow management system, with the workflow management system mediating communication with the cloud. For example, LATTICE may have APIs for every unique device, such as a Zeiss Cirrus Optical Coherence Tomography imaging system as distinct from a Heidelberg Spectral is Optical Coherence Tomography imaging systems, as further distinct from and Optos Optomap Widefield Fundus imaging system that includes specific instructions for that device. In some embodiments, an indicator may be set in a data field that tells the system which API should be used. In some embodiments, the APIs may be stored at the pre-processing engine 706 so that the APIs can be timely updated. However, in certain embodiments the API may be provided as an application without departing from the scope of the present inventive concept.

The pre-processing engine 706 is not limited to just anonymizing (de-identifying the data). The pre-processing engine 706 is configured to receive the raw images and data from the workflow management module, determine a specific set of instructions (as discussed above) associated with the received raw images and data from the workflow management module; and process the received raw images and data based on the specific set of instructions associated with the received raw images and data from the workflow management module. The data may be validated, quantified, annotated, classified, anonymized and undergo other pre-processing steps in accordance with embodiments discussed herein before being distributed to the cloud storage module 707. As discussed above, the data stored in the cloud storage module 707 is de-identified and unstructured, i.e., no folders, subfolders and the like.

As discussed above, when the data is de-identified, a key 709 is created, which remains outside the cloud. The key may be created in the pre-processing engine, but it is stored separately from the data itself. Some embodiments of the present inventive concept contain a pollution control function/module that includes a list of rules that removes all "non-essential" data. Whether the data is essential or non-essential can be determined on a case by case basis. The data that is removed may not be discarded or recycled, but kept, until a user indicates with the data should be stored, discarded or the like.

The pre-processing engine 706 allows complete control and providence over the data. The pre-processing engine can be viewed like a mailbox. A user provides the data and the pre-processing engine 706 anonymizes, restructures and the like and puts the data where it is supposed to go, for example, in the cloud or back in the structured database. It is advantageous to store the data in both structured and unstructured databases as some data lends itself to structured databases and other types of data lends itself to unstructured data. For example, images lend themselves to unstructured formats. If you put images in folders, you may not find the specific data/image you are looking for unless the specific search is performed.

As discussed above, the cloud may include various modules that can access the data stored in the cloud storage module 707 and used that data for various purposes. For example, one module in communication with the cloud storage module 707 may be configured to apply a set of rules to at least a portion of the images and data stored in the cloud storage module (methods and algorithms). This list of rules may be an algorithm. This same module or a different module may be configured to apply a series of algorithms (a recipe) to at least a portion of the images and data stored in the cloud storage module. Another module may be configured to use at least a portion of the images and data stored in the cloud storage module and derive new images and data therefrom (derivation module or algorithmically derived data). For example, the derivation module may be configured to, for example, assess quality of the images and data; reduce noise in the images and data; segment the images and data; and/or measure the images and data.

As further illustrated in FIG. 7, other modules may include modules directed to research documentation, operation history and the like without departing from the scope of the present inventive concept. As illustrated by the circular arrangement of the modules in FIG. 7 (as well as FIGS. 4 and 5 discussed above). The images and data stored in the cloud storage module are constantly updated by various modules in the cloud. In other words, the data is reused and replicates and derived data modified over and over (with the original data preserving full original provenance). In some embodiments, the modules in the cloud utilize one or more of artificial intelligence (AI), statistical abstraction; image abstraction and image extraction to provide derived data. In some embodiments, one of the modules in the cloud is provided by MOSAIC. The images and data stored in the cloud storage module 707 may include, for example, statistical data; processed images; reduced images; retrospective images; in vivo images; in vitro images; functional test results; and biospecimen test results.

The system's ability to maintain complete traceability (Operation History), i.e., maintaining the providence of all the data is advantageous. In other words, any data can be recreated, backwards and forwards and, thus, the raw image can always be recreated. As discussed above, in some embodiments of the present inventive concept, one or more aspects of may be stored in the blockchain. Use of the blockchain will enable the traceability feature of all operations on the data as well as simplify regulatory audits. Furthermore, the blockchain may also enable keeping a record of anyone who has accessed the data or has access to the data. If an unauthorized person sees the data, takes the data or is given the data, the system records this information for a user's consumption.

As discussed above, some embodiments of the present inventive concept use MOSAIC to process data, for example, randomize, segment and the like. In some embodiments, MOSAIC may be used to create new algorithms and recipes and push them into the module for algorithms and recipes in the cloud. However, it will be understood that embodiments of the present inventive concept are not limited to this configuration.

In some embodiments, the image and data bank includes ophthalmic images and data, however, it will be understood that embodiments of the present inventive concept are not limited to this configuration. Any type of images and data may be used without departing from the scope of the present inventive concept.

As discussed above, some embodiments of the present inventive concept provide an integrated system for collecting, managing and mining images and data that may be regularly updated and refined and using the images and data together with any of the subsequently derived data for the training, testing, and validation of algorithms. These algorithms may be used, for example, for the development of markers of disease and disease progress, markers of physiological response to internal and external factors including therapeutic interventions, correlation of phenotypes with genotypes, and development of diagnostic and prognostic measurements and methodologies.

Figure 8:
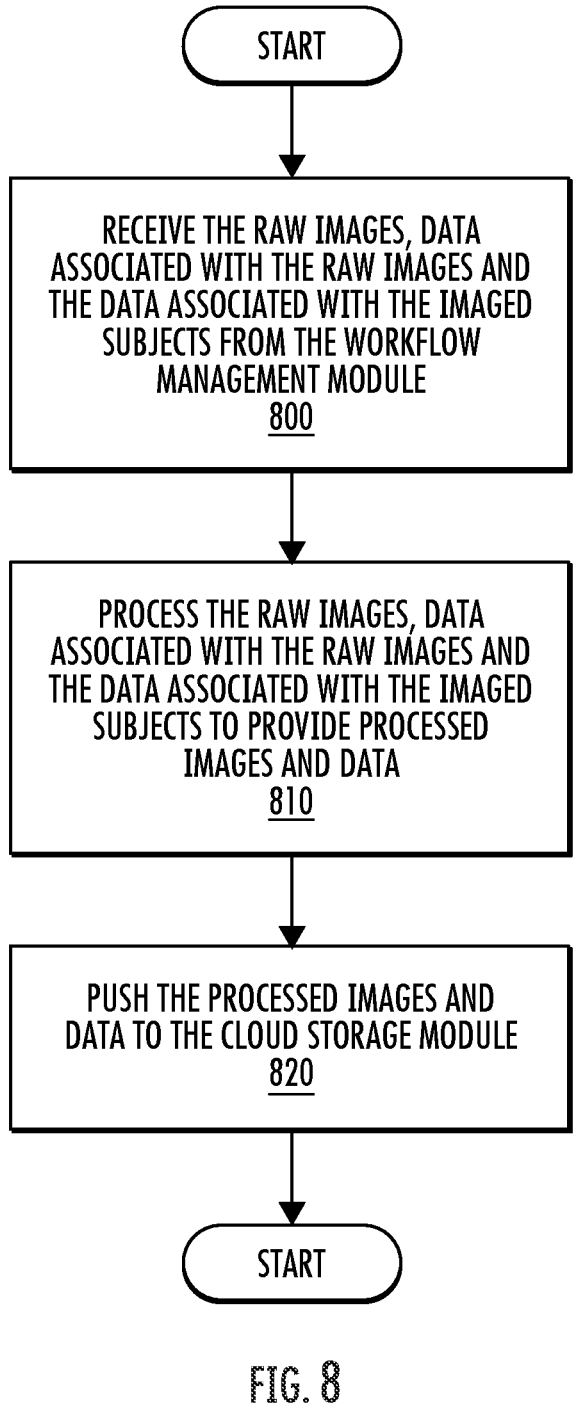
FIG. 8 is a flowchart illustrating operations in accordance with some embodiments of the present inventive concept.

Referring now to the flowchart of FIG. 8, high level operation for a processing data at a pre-processing engine will be discussed. The operations illustrated in the flowchart of FIG. 8 are directed to a method for processing and using images in a system. The system including an image and data bank including a plurality of raw images and associated data; a workflow management module in communication with the image and data bank and configured to manage and analyze the raw images and data in the image and data bank and a cloud storage module in a cloud configured to store the images and data from the workflow management module. Operations begin at block 800 by receiving the images and data from the workflow management module. As discussed above, structured data is stored at a private site in the system. The workflow management module (LATTICE) processes the data and forwards the structure data to a pre-processing engine. The pre-processing engine processes the images and data before the images and data are pushed into the cloud storage module (blocks 810 and 820). The cloud storage module is configured to receive the processed images and data. At a minimum, processing the data includes anonymizing the images and data to provide de-identified data to the cloud storage module and creating a key that remains separate from the processed images and data. The key allows the images and data to maintain traceability both forward and backward.

The pre-processing engine may receive the raw images and data from the workflow management module; determine a specific set of instructions associated with the received raw images and data from the workflow management module; and process the received raw images and data based on the specific set of instructions associated with the received raw images and data from the workflow management module. The specific set of instructions associated with the received raw images and data may be determined by an indicator set in a data field. The indicator may identify a specific set of instructions for the received raw images and data from a particular device.

In some embodiments, the pre-processing engine may remove non-essential or private data from the raw images and data; store the removed non-essential or private data; and, before recycling the non-essential or private data, request permission from a user associated with the raw images and data. The rules for this anonymization may be prevailing HIPAA rules (USA), GDPR rules (EU), and the like, and the set of rules applied may be themselves stored as traceable data elements, such that data may be re-anonymized as rules change over time.

After the data is processed and pushed to the cloud, the data may be used by various modules, the modules may apply a set of rules to at least a portion of the images and data stored in the cloud storage module; apply a series of algorithms to at least a portion of the images and data stored in the cloud storage module; and/or using at least a portion of the images and data stored in the cloud storage module to derive new images and data therefrom.

As further discussed above, the data is constantly being updated, thus, the steps of the method are repeated to constantly provide updated images and data.

Figure 9:
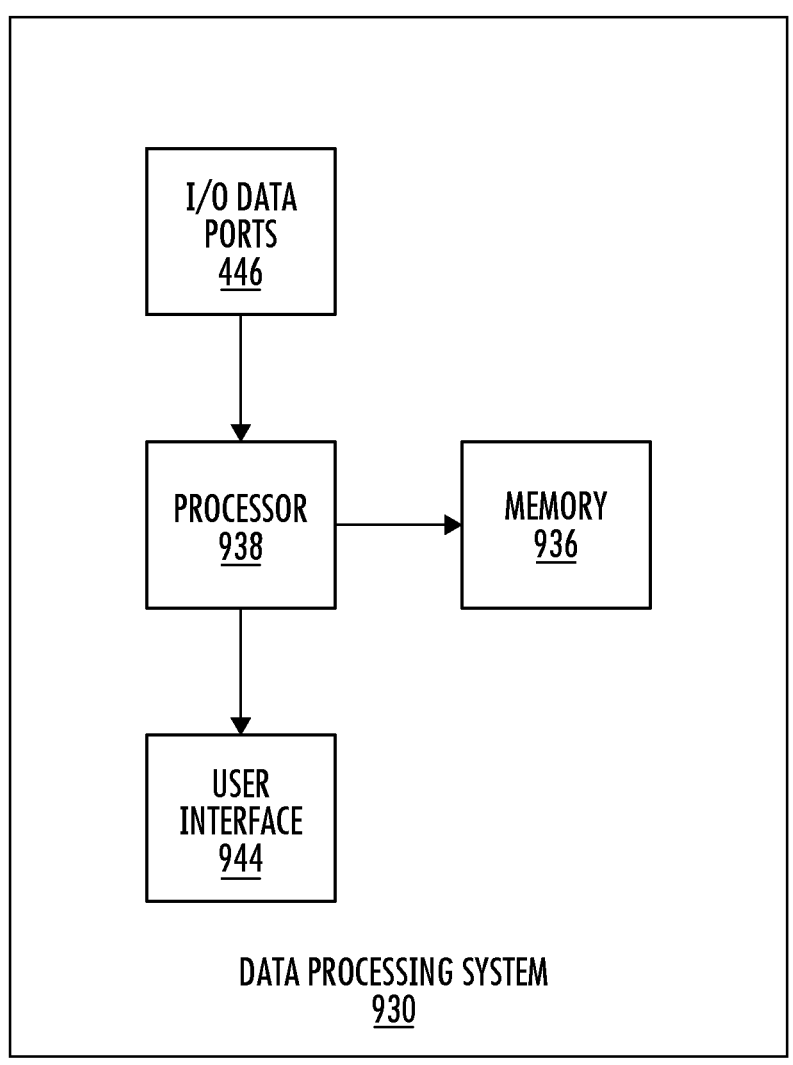
FIG. 9 is a block diagram of a data processor in accordance with some embodiments of the present inventive concept.

As is clear from the embodiments discussed above, some aspects of the present inventive concept may be implemented by a data processing system. The data processing system may be included at any module of the system without departing from the scope of the preset inventive concept. Exemplary embodiments of a data processing system 930 configured in accordance with embodiments of the present inventive concept will be discussed with respect to FIG. 9. The data processing system 930 may include a user interface

944, including, for example, input device(s) such as a keyboard or keypad, a display, a speaker and/or microphone, and a memory 936 that communicate with a processor 938. The data processing system 930 may further include I/O data port(s) 946 that also communicates with the processor 938. The I/O data ports 946 can be used to transfer information between the data processing system 930 and another computer system or a network using, for example, an Internet Protocol (IP) connection. These components may be conventional components such as those used in many conventional data processing systems, which may be configured to operate as described herein.

In the drawings and specification, there have been disclosed exemplary embodiments of the inventive concept. However, many variations and modifications can be made to these embodiments without substantially departing from the principles of the present inventive concept. Accordingly, although specific terms are used, they are used in a generic and descriptive sense only and not for purposes of limitation, the scope of the inventive concept being defined by the following claims.

That which is claimed is:

1. An integrated system for processing and using images acquired of subjects in a research or clinical environment, the integrated system comprising:

an image and data bank including source images and data that includes a plurality of raw images originating from one or more image-generating devices, data associated with the raw images, and data associated with imaged subjects;

a workflow management module in direct communication with the image and data bank, the workflow management module being configured to manage and analyze the source images and data that includes the plurality of raw images, data associated with the raw images and the data associated with the imaged subjects in the image and data bank; and a cloud storage module in a cloud configured to execute instructions from the workflow management module to operate on the source images and data contained in the image and data bank, and store anonymized results derived from an operation traceable to the source images and data, wherein a first level of deidentified traceability between source images, subjects, and derived results is preserved that restricts access to private subject information; and wherein a second level of traceability to private subject information is preserved that requires additional permissions; and wherein the first level of deidentified traceability and the second level of traceability to private subject data is preserved across subsequent operations on the source images, subjects and derived data initiated through the workflow management module.

\* \* \* \* \*